United States Patent [19]  [11] 4,318,852
Heitman et al.  [45] Mar. 9, 1982

[54] SODIUM AMOXICILLIN SOLVATE

[75] Inventors: Herwarth Heitman, Zoetermeer; Johannes K. van der Drift, Delft; Everardus J. A. M. Leenderts, Rhoon; Herman H. Grootveld, Benthuizen, all of Netherlands

[73] Assignee: Gist-Brocades N.V., Delft, Netherlands

[21] Appl. No.: 257,747

[22] Filed: Apr. 27, 1981

[30] Foreign Application Priority Data

May 8, 1980 [NL] Netherlands ............... 8002636

[51] Int. Cl.$^3$ ............... C07D 499/44; A61K 31/43
[52] U.S. Cl. ............... 260/239.1; 424/271
[58] Field of Search ............... 260/239.1

[56] References Cited

U.S. PATENT DOCUMENTS

| | | | |
|---|---|---|---|
| 3,926,958 | 12/1975 | Callander | 260/239.1 |
| 4,014,868 | 3/1977 | Berry et al. | 260/239.1 |
| 4,035,381 | 7/1977 | Kaplan et al. | 260/245.2 R |
| 4,048,158 | 9/1977 | Sugimoto et al. | 260/239.1 |
| 4,254,029 | 3/1981 | Kaspi et al. | 260/239.1 |

Primary Examiner—G. T. Breitenstein
Attorney, Agent, or Firm—Hammond & Littell, Weissenberger and Muserlian

[57] ABSTRACT

The solvate of sodium amoxicillin and N-methyl-2-pyrrolidone and its preparation which is a stable antibiotic from which injectable solutions may be prepared.

1 Claim, No Drawings

SODIUM AMOXICILLIN SOLVATE

STATE OF THE ART

The literature, especially the recent patent literature, shows that great efforts are being made to find amoxicillin preparations that are sufficiently stable in dry form and that provide a suitable starting material for stable injectable solutions. The literature also shows that the chemical and physical properties of amoxicillin differ from those of semi-synthetic penicillins known before to such a degree that the methods commonly used for those penicillins generally cannot be applied to prepare injectable preparations of amoxicillin.

The suggested solutions include modified preparations prepared from the usual alkali metal salts of amoxicillin as well as the use of salts with different cations. One method to obtain an amoxicillin preparation by freeze-drying that can be constituted into an injectable preparation is described in Dutch patent application Ser. No. 77-07494. According to this application, sodium amoxicillin is freeze-dried in an aqueous solvent system to which a secondary or tertiary alkanol with four or five carbon atoms has been added as a stabilizer.

Dutch patent application Ser. No. 75-09701 discloses a process for the preparation of the choline salt and the N-methyl-D-glucamine salt of amoxicillin, whereas in Dutch patent application Ser. No. 75-09698, the preparation of the arginine salt of amoxicillin is described whereby the said salts of amoxicillin would result in new non-toxic amoxicillin preparations for parenteral administration with preservation of the antibiotic activities. It is also stated in this patent application that neither amoxicillin as such nor the salts known so far can be administered satisfactorily by the parenteral route. Japanese published application Ser. No. 51032723 (Kokai) discloses the preparation of a suitable injectable solution comprising amoxicillin and the sodium salt of glycine.

German Offenlegungsschrift No. 2540523 discloses a process for the preparation of salts of D-α-carboxyamino-p-hydroxybenzyl penicillin intended for the preparation of satisfactorily injectable amoxicillin compositions and it is stated here explicitly that the preparation of injectable preparations of amoxicillin was found to be much more difficult than initially anticipated due to the decomposition of amoxicillin salts in aqueous solutions. According to the said Offenlegungsschrift, mixtures of the sodium salt of amoxicillin and the disodium salt of D-α-carboxyamino-p-hydroxybenzyl penicillin should preferably be used.

Dutch patent application Serial No. 76-02180 describes a process for the preparation of a stable preparation of amoxicillin from which stable injectable preparations can be prepared that are well tolerated on administration. This preparation consists of a powder that is easily constituted into an injectable preparation by addition of an aqueous vehicle and the powder consists of minute particles of amoxicillin trihydrate coated with a dispersion agent with the ratio of amoxicillin trihydrate to dispersion agent being from 1000:1 to 20:1. The minute particles should have a mean diameter of $2\mu$ to $20\mu$ and at least 95% of them should have a diameter between $0.5\mu$ and $50\mu$, whereas 10 to 100% of the surface should be coated with the dispersion agent.

For similar reasons, research has been directed to amoxicillin derivatives which yield amoxicillin on decomposition in the body. This principle is illustrated by U.S. Pat. No. 4,035,381 and Dutch patent application Ser. No. 77-01480.

The preparation of solvates of alkali metal or alkaline earth metal salts of amoxicillin with amides is described in Dutch patent application Ser. No. 74-06420. Preferred amides are those with the formula RCONR'R" in which R is hydrogen or methyl and R' and R" each is hydrogen or methyl or ethyl and urea. The examples show that only dimethylformamide and dimethyl-acetamide have been actually used. In the preparation of the solvates, amoxicillin trihydrate serves as a starting material which is dehydrated first by treatment with an alkanol. This requires considerable time of stirring which results in a gelatinous product that is difficult to handle. According to three of the four examples, a diethylamine salt is formed first and this is subsequently converted into the sodium salt but the solvates formed with amides are not always well defined products with a constant composition.

OBJECTS OF THE INVENTION

It is an object of the invention to provide the novel stable solvate of sodium amoxicillin and N-methyl-2-pyrrolidone which has a well-defined, constant composition and its preparation.

It is another object of the invention to provide novel antibiotic compositions and to provide a novel method of treating bacterial infections in warm-blooded animals.

These and other objects and advantages of the invention will become obvious from the following detailed description.

THE INVENTION

The novel product of the invention is the solvate of sodium amoxicillin and N-methyl-2-pyrrolidone which is a stable, well-defined, crystalline product having a constant composition which is suited to be constituted into a useful injectable preparation.

According to the novel process of the invention, the said solvate is prepared by reacting amoxicillin with a solution of a source of sodium ions and subsequently causing the solvate to crystallize in the presence of N-methyl-2-pyrrolidone by addition of one or more organic solvents to the mixture.

The reaction between amoxicillin and the source of sodium ions is preferably carried out in a polar organic solvent and the reaction may, for instance, suitably be carried out in N-methyl-2-pyrrolidone or a mixture thereof with a polar organic solvent. A suitable solvent mixture is a mixture of N-methyl-2-pyrrolidone with a lower alcohol such as ethanol. The term "lower alcohol" here refers to an alcohol with 1 to 6 carbon atoms.

The reaction and the crystallization are preferably carried out at a temperature between $-10°$ and $40°$ C., preferably between $0°$ and $25°$ C. Suitable sources of sodium ions are sodium compounds already known from the preparation of other semi-synthetic penicillins but sodium 2-ethylhexanoate is preferably used but other useful examples of sources of sodium ions are sodium ethoxide, sodium hydroxide, sodium carbonate and sodium bicarbonate. If desired, the ethylhexanoate can be prepared in situ from the base and the acid.

Various organic solvents can be used to effect crystallization of the solvate. Solvents already known in the preparation of penicillin salts are generally suitable for the purpose. Preferred solvents are halogenated hydrocarbons such as dichloromethane and 1,2-dichloroethane, esters such as ethyl acetate and methyl acetate, alcohols like ethanol and propanol-2 and nitriles such as acetonitrile. In a most preferred feature of the invention, an amount of ethanol is added first and then propanol-2 is added.

The invention also includes the preparation of injectable compositions from the solvate of sodium amoxicillin and N-methyl-2-pyrrolidone by a method customarily employed in pharmacy. The injectable composition may, for instance, be prepared by adding distilled, sterile, pyrogen-free water and other optional auxiliary substances to the dry solvate and sterilizing the resulting solution by the ususal method. Alternatively, a sterile solvate is prepared by sterile filtration and the said solvate is made into an injectable solution under aseptic conditions.

Examples of suitable amoxicillin concentrations in the injectable liquid are 200 and 50 mg/ml, respectively for intramuscular and intravenous administration. Suitable dosages of amoxicillin for parenteral administration in adult humans range from 750 to 4500 mg daily.

In the following examples, there are described several preferred embodiments to illustrate the invention. However, it should be understood that the invention is not intended to be limited to the specific embodiments.

EXAMPLE 1

48.5 ml (304 mmole) of 2-ethylhexanoic acid were dissolved in 150 ml of N-methyl-2-pyrrolidone and 11.1 g (278 mmole) of sodium hydroxide are added to this solution. The mixture was stirred for at least 8 hours under anhydrous conditions after which 150 ml of N-methyl-2-pyrrolidone were added thereto. 100 g (238 mmole) of amoxicillin trihydrate were added at 10° C. to the resulting solution and after stirring the mixture for one hour, the solution was filtered. Some seed crystals were added to the solution and then 335 ml of dichloromethane were added dropwise at 20° C. over the course of 1½ hours. The precipitate obtained was isolated by filtration and repeatedly was washed with mixtures of N-methyl-2-pyrrolidone and dichloromethane with an increasing content of dichloromethane and finally with dichloromethane. The product was dried in vacuo at 30° C. to a constant weight to obtain a yield of 95 g (81.9%) of the desired solvate which contained 73.1% of amoxicillin (calculated as the free acid), 20% of N-methyl-2-pyrrolidone, 0.7% of dichloromethane, 1.2% of decomposition products and 0.9% of water.

EXAMPLE 2

The procedure of Example 1 was repeated with replacement of the dichloromethane with 400 ml of ethyl acetate and the yield was 98 g (84.5%) of solvate which contained 72.2% of amoxicillin (calculated as the free acid), 21% of N-methyl-2-pyrrolidone, 0.5% of ethyl acetate, 0.5% of decomposition products and 0.7% of water.

EXAMPLE 3

The procedure of Example 1 was repeated with replacement of the dichloromethane with 300 ml of ethanol and the yield was 44 g (38%) of solvate which contained 73.7% of amoxicillin (calculated as the free acid), 20% of N-methyl-2-pyrrolidone, 2% of ethanol, 0.5% of decomposition products and 0.4% of water. The non-crystallized amoxicillin could be recovered in a simple way as the trihydrate.

EXAMPLE 4

The procedure of Example 1 was repeated with replacement of the dichloromethane with 400 ml of acetonitrile and the yield was 91 g (78.4%) of solvate which contained 73.1% of amoxicillin (calculated as the free acid), 20% of N-methyl-2-pyrrolidone, 1% of acetonitrile, 0.8% of decomposition products and 0.3% of water.

EXAMPLE 5

The procedure of Example 1 was repeated with replacement of dichloromethane with 450 ml of propanol-2 and the yield was 63 g (54.3%) of solvate which contained 70.3% of amoxicillin (calculated as the free acid).

EXAMPLE 6

11.1 g (278 mmole) of sodium hydroxide were added to a mixture of 100 ml of absolute ethanol and 48.5 ml (304 mmole) of 2-ethylhexanoic acid and the resulting mixture was refluxed for one hour and then cooled to 10° C. 200 ml of N-methyl-2-pyrrolidone and 70 g (166.9 mmole) of amoxicillin trihydrate were added to the mixture and after stirring for about 45 minutes at a temperature of 10° to 20° C., the clear solution was filtered. The filter was washed with 50 ml of N-methyl-2-pyrrolidone. The filtrate was seeded by addition of crystals and then 150 ml of absolute ethanol were added dropwise at 20° C. over 1½ hours. Then, 400 ml of propanol-2 were added thereto over 90 minutes after which the solution was stirred for two hours at about 20° C. The precipitate obtained was isolated by filtration and was washed with 100 ml of a 1—1 mixture of N-methyl-2-pyrrolidone and absolute ethanol and finally with absolute ethanol. The product was dried in vacuo at 30° C. to a constant weight to obtain 63 g (77.6%) of solvate which contained 74.2% of amoxocillin (calculated as the free acid), 19% of N-methyl-2-pyrrolidone, 2% of ethanol, 0.3% of propanol-2 and 0.4% of water.

The amoxicillin content was determined by the ferri hydroxamate method and the percentage of decomposition products was determined by mercurimetric titration. The percentages of N-methyl-2-pyrrolidone and other solvents were determined by means of NMR spectroscopy and gas chromatography while the water content was determined by the method of Karl Fischer.

The analysis results show that in the product obtained the molecular ratio of amoxicillin: N-methyl-2-pyrrolidone always is approximately 1:1. X-ray diffraction of the crystals confirmed that the substance contains only one type of crystal. The X-ray photographs of the substances obtained according to the various Examples were nearly identical.

The following Table shows, by way of example, the results obtained with the substance prepared in Example 3.

TABLE

| d | I | d | I |
|---|---|---|---|
| 10.0 | 2 | 3.91 | 1 |
| 9.4 | 1 | 3.79 | 1B |
| 9.0 | 8 | 3.77 | 1 |
| 7.6 | 4 | 3.70 | 4 |
| 6.4 | 1 | 3.59 | 1 |
| 6.2 | 1 | 3.55 | 2 |
| 5.75 | 10B | 3.44 | 1 |
| 5.6 | 6 | 3.33 | 2 |
| 5.4 | 4 | 3.17 | 1B |

TABLE-continued

| d | I | d | I |
|---|---|---|---|
| 5.1 | 6 | 3.11 | 3 |
| 5.0 | 2B | 3.04 | 1 |
| 4.6 | 1 | 3.00 | 1 |
| 4.4 | 2 | 2.93 | 3 |
| 4.25 | 1B | 2.88 | 1 |
| 4.00 | 1 | 2.13 | 1 | d = distance between lattice planes in Angstrom
I = intensity (range 1–10)
B = line is broader than normal Lines with an intensity less than 0.7 were omitted. From the above data, it can be calculated that the substance is monoclinic with the following unit cell dimensions:

$a = 20.1077$ Å
$b = 10.1127$ Å
$c = 11.6451$ Å
$\beta = 98.60°$

A number of preparations were stored from one to three weeks in tightly closed bottles at 65° C. and examination showed that significant changes in amoxicillin content and the percentage of decomposition products did not occur.

Various modifications of the product and processes of the invention may be made without departing from the spirit or scope thereof and it is to be understood that the invention is intended to be limited only as defined in the appended claims.

What is claimed is:

1. The solvate of sodium amoxicillin and N-methyl-2-pyrrolidone.

* * * * *